United States Patent
Barak et al.

(12) 
(10) Patent No.: US 6,492,426 B1
(45) Date of Patent: Dec. 10, 2002

(54) USE OF 1-AMINOINDAN DERIVATIVES FOR TREATMENT OF MANIA IN BIPOLAR MOOD DISORDER

(75) Inventors: Gabriela Barak, Jerusalem (IL); Ruth Levy, Tel-Aviv (IL)

(73) Assignee: Teva Pharmaceutical Industries, Ltd. (IL)

( * ) Notice: Subject to any disclaimer, the term of this patent is extended or adjusted under 35 U.S.C. 154(b) by 0 days.

(21) Appl. No.: 09/699,127

(22) Filed: Oct. 27, 2000

Related U.S. Application Data

(60) Provisional application No. 60/161,817, filed on Oct. 27, 1999.

(51) Int. Cl.$^7$ .................. A61K 31/16; A61K 31/165
(52) U.S. Cl. .................. 514/629; 514/617; 514/619; 514/613; 514/625
(58) Field of Search .................. 514/613, 617, 514/619, 629, 625

(56) References Cited

U.S. PATENT DOCUMENTS

| | | |
|---|---|---|
| 3,637,740 A | 1/1972 | Sarges |
| 3,886,168 A | 5/1975 | Himmele et al. |
| 4,096,173 A | 6/1978 | Molloy |
| 4,788,130 A | 11/1988 | Oshiro et al. |
| 4,792,628 A | 12/1988 | Oshiro et al. |
| 4,882,339 A | 11/1989 | Wasley |
| 4,895,847 A | 1/1990 | Oshiro et al. |
| 5,055,474 A | 10/1991 | Oshiro et al. |
| 5,242,919 A | 9/1993 | Oshiro et al. |
| 5,344,836 A | 9/1994 | Hamanaka et al. |
| 5,387,612 A | 2/1995 | Youdim et al. |
| 5,424,303 A | 6/1995 | Phan et al. |
| 5,453,446 A | 9/1995 | Youdim et al. |
| 5,457,133 A | 10/1995 | Youdim et al. |
| 5,486,541 A | 1/1996 | Sterling et al. |
| 5,519,061 A | 5/1996 | Youdim et al. |
| 5,532,415 A | 7/1996 | Youdim et al. |
| 5,576,353 A | 11/1996 | Youdim et al. |
| 5,599,991 A | 2/1997 | Youdim et al. |
| 5,639,913 A | 6/1997 | Lidor et al. |
| 5,646,188 A | 7/1997 | Gilad et al. |
| 5,656,642 A | 8/1997 | Fujioka et al. |
| 5,668,181 A | 9/1997 | Youdim et al. |
| 5,744,500 A | 4/1998 | Youdim et al. |
| 5,760,058 A | 6/1998 | Fujioka et al. |
| 5,786,390 A | 7/1998 | Youdim et al. |
| 5,877,218 A | 3/1999 | Herzig et al. |
| 5,877,221 A | 3/1999 | Cohen et al. |
| 5,880,159 A | 3/1999 | Herzig et al. |
| 5,887,218 A | 3/1999 | Herzig et al. |
| 5,887,221 A | 3/1999 | Cohen et al. |
| 5,891,923 A | 4/1999 | Youdim et al. |
| 5,914,349 A | 6/1999 | Cohen et al. |
| 5,994,408 A | 11/1999 | Cohen et al. |
| 6,060,464 A | 5/2000 | Nguyen et al. |
| 6,126,968 A | 10/2000 | Peskin et al. |
| 6,136,826 A | 10/2000 | Fujioka et al. |
| 6,251,938 B1 | 6/2001 | Chorev et al. |
| 6,227,886 B1 | 8/2001 | Levy et al. |
| 6,271,263 B1 | 8/2001 | Sklarz et al. |
| 6,303,650 B1 | 10/2001 | Chorev et al. |
| 6,316,504 B1 | 11/2001 | Youdim et al. |

FOREIGN PATENT DOCUMENTS

| | | |
|---|---|---|
| EP | 0436492 | 7/1991 |
| EP | 0538134 | 4/1993 |
| GB | 852735 | 11/1960 |
| WO | 9511016 | 4/1993 |
| WO | 9518617 | 7/1995 |
| WO | 9855447 | 12/1998 |

OTHER PUBLICATIONS

Horn and Snyder, "Steric Requirements for Catecholamine Uptake by Rat Brain Synaptosomes: Studies with Rigid Analogs of Amphetamine," *J. Pharmacol. Exp. Ther.*, 1972, 180 (3): 523–530.

Martin et al., "Potential Anti–Parkinson Drugs Designed by Receptor Mapping," 1973, *J. Med. Chem.*, 16 (2): 147–150.

(List continued on next page.)

*Primary Examiner*—Rebecca Cook
(74) *Attorney, Agent, or Firm*—John P. White; Cooper & Dunham LLP

(57) ABSTRACT

The subject invention provides a method of treating mania in bipolar disorder in a subject comprising administering to the subject a therapeutically effective amount of derivatives of 1-aminoindan or their racemic mixtures, enantiomers, or salts, of the general formula:

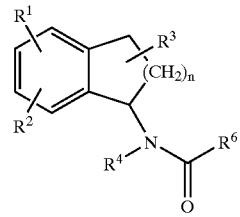

wherein n is 0 or 1;

each of $R^1$ and $R^2$ are hydrogen, $C_1$–$C_4$ alkyl, halogen;

$R^3$ is hydrogen, $C_1$–$C_4$ alkyl, hydroxy, $C_1$–$C_4$ alkoxy;

$R^4$ is hydrogen, $C_1$–$C_4$ alkyl;

$R^6$ is hydrogen, substituted or unsubstituted $C_1$–$C_{12}$ alkyl, $C_6$–$C_{12}$ aryl, $C_7$–$C_{12}$ aralkyl or A—N—$R^9R^{10}$, provided that $R^6$ is not methyl when $R^1$, $R^2$, $R^3$ and $R^4$ are hydrogen atoms, wherein A is substituted or unsubstituted $C_1$–$C_{12}$ alkyl, substituted or unsubstituted $C_6$–$C_{12}$ aryl, substituted or unsubstituted $C_7$–$C_{12}$ aralkyl, and each of $R^9$ and $R^{10}$ are independently hydrogen, $C_1$–$C_{12}$ alkyl, $C_6$–$C_{12}$ aryl, $C_7$–$C_{12}$ aralkyl, COOtBu, or indanyl;

and racemic mixtures, enantiomers, and salts thereof.

20 Claims, 5 Drawing Sheets

OTHER PUBLICATIONS

Martin et al., "Discriminant Analysis of the Relationship between Physical Properties and the Inhibition of Monoamine Oxidase by Aminotetralins and Aminoindans," 1974, *J. Med. Chem.*, 17 (4): 409–413.

Oshiro et al., "Novel Cerebroprotective Agents with Central Nervous System Stimulating Activity. 1. Synthesis and Pharmacology of 1–Amino–7–hydroxyindan Derivatives," 1991, *J. Med. Chem.*, 34 (7): 2004–2013.

Oshiro et al., "Novel Cerebroprotective Agents with Central Nervous System Stimulating Activity. 2. Synthesis and Pharmacology of the 1–(Acylamino)–7–hydroxyindan Derivatives," 1991, *J. Med. Chem.*, 34 (7): 2014–2020.

Huebner et al., "N–methyl–N–(2–propynyl)–1–indanamine. A Potent Monoamine Oxidase Inhibitor," *J. Med. Chem.* (1960) 9(6): 830–832.

Chermann et al., "Preparation and formulation of dihydrocyclopenta (b) thiophenes and analogs as antiviral agents," Chem. Abstracts (2002) 120:106749.

Matsuo et al., "Preparation of fluoroalkyl aromatic compounds as intermediates for agrochemicals and pharmaceuticals," Chem. Abstracts (2002) 109:128541.

1

2

3

4

USE OF 1-AMINOINDAN DERIVATIVES FOR TREATMENT OF MANIA IN BIPOLAR MOOD DISORDER

This application claims the benefit of U.S. Provisional Application No. 60/161,817, filed Oct. 27, 1999.

Throughout this application, various references are identified by authors and full citations. Disclosures of these publications in their entireties are hereby incorporated by reference into this application to more fully describe the state of the art to which this invention pertains.

BACKGROUND OF THE INVENTION

Bipolar mood disorder commonly begins with depression and is characterized by at least one elated period sometime during the course of the illness. In bipolar I disorder, full blown manic and major depressive episodes alternate. In bipolar II disorder, depressive episodes alternate with hypomanias (i.e., mild, nonpsychotic periods of excitement) of relatively short duration. Although insomnia and poor appetite do occur during the depressive phase of bipolar illness, such atypical depressive signs as hypersomnia and overeating are more characteristic and may recur on a seasonal basis (e.g., in the autumn or winter).

In full blown manic psychosis, the mood typically is one of elation, but irritability and frank hostility are not uncommon. The patient's lack of insight and inordinate capacity for activity lead to a dangerously explosive psychotic state, in which the individual is impatient, intrusive, and meddlesome and responds with aggressive irritability when crossed. Interpersonal friction results and may lead to secondary paranoid delusional interpretations of being persecuted. Audio and visual hallucinations are sometime present, occur at the high mania, and are usually understandably linked with the morbid mood. The need for sleep is decreased. Manic persons are inexhaustibly, excessively, and impulsively involved in various activities without recognizing the inherent social dangers.

Mixed states are labile mixtures between depressive and manic manifestations or rapid alternation from one state to the other and commonly occur in manic depressive at one time or another. (The Merck Manual 16$^{th}$ edition, 1992, p. 1592, 1593, 1599) Bipolar disorder (BP) affects 1–2% of the population.

The classical psychopharmaceuticals effective in the treatment of mood disorders can be grouped into three classes: the heterocyclic anti depressants (HCA), monoamine oxidase inhibitors (MAOI) and lithium salts. (Merck, p. 1603). While HCA and MAOI drugs are indicated for the depressive phase of the bipolar disorder, lithium is known to attenuate the bipolar mood swings.

Only around 70% of the patients are considered to respond to the treatment with HCA or lithium drugs (Merck, p. 1604, 1607). For the resistant and refractory disease, combinations of drugs are used, increasing even more the panel of characteristic side effects.

In light of this situation, there is a continuous search for new drugs aimed to solve the problems of drug resistance and severe side effects. Lately, drugs like valproic acid, carbamazepin, verapamil, propanolol, clonidine and adenyl cyclase inhibitors have been found to be beneficial either alone or as adjunct therapy for manic patients. (O. Kaufman and R. H. Belmaker, P. Soubrie, ed.: Anxiety, Depression and Mania. Anim. Models Psychiatr. Disord., Basel, Karger, 1991, 3, pp. 103–121).

In order to discover new drugs, rodent models relevant to the manic phase, like amphetamine, amphetamine with chlordiazepoxide, morphine or desmethylimipramine induced hyperactivity or to the depression phase like immobilizations, are usually used (D. L. Murphy, Anim. Mod. Psych. Neur., 1977, pp. 211–225).

These mania models focus on an induced increase in the activity level of the animal (e.g., locomotor or/and vertical activity) as a parallel to the hyperactivity of the maniac patient. The reversal of the induced hyperactivity in rodents by their pretreatment with a drug of interest indicates the possible efficacy of this drug in the treatment of human mania.

A variety of substituted 1-aminoindans have been proposed to have some activity in the central nervous system (CNS). This group of compounds has a wide range of activities, for example, U.S. Pat. No. 4,096,173 discloses 1-aminoindans with ring chloro substituents as having anti-allergic, anti-spasmodic and local anesthetic activities, whereas U.S Pat. No. 3,886,168 discloses the anti-inflammatory and vasodilatory activity of certain 1-aminoindans.

It is hypothesized therein that the activity may be based in the CNS though no evidence is provided or suggested to support the hypothesis. British Patent No. 852,735 discloses 1-aminoindans with a lower alkoxy group in the five position as being active in dilating coronary blood vessels.

U.S. Pat. No. 3,637,740 discloses dl-1-N,N-dimethylamino-4-methoxy-7-chloroindane as an antidepressant and/or an antianxiety agent. However, no clear evidence is provided of either activity.

Horne et al. (J. Pharm. Exp. Ther. 1972, 180(3), p. 523) have shown that 2-aminoindan is a far superior inhibitor of catecholamine uptake than 1-aminoindan and therefore dismissed the latter as a candidate for use in the treatment of Parkinson's Disease. Martin et al. (J. Med. Chem. 1973, 16(2), p. 147; J. Med. Chem. 1974, 17(4), p. 409) describe experiments wherein N-methyl-5-methoxy derivatives of 1-aminoindan are investigated as having monoamine oxidase (MAO) inhibitory activity.

Oshiro et al. (J. Med. Chem. 1991, 34, pp. 2004–2013) disclose a wide range of 7-hydroxy-1-aminoindan derivatives that they subjected to screening for use as cerebroprotective agents using an antihypoxic test and as CNS stimulatory agents using a cerebral trauma test. In the resultant structure-activity-analysis, it was found that replacement of the 7-hydroxy group by a methoxy group resulted in loss of activity in the antihypoxic test but not in the cerebral trauma test. Their conclusion was that the 7-hydroxy is essential to obtain the desired activity. This is evident from their subsequent paper wherein a broader range of 7-hydroxy derivatives are screened (J. Med. Chem. 1991, 34, 2014–2020). These 7-hydroxy-1-aminoindans are defined in U.S. Pat. Nos. 4,788,130; 4,792,628; 4,895,847; 5,055,474; and 5,242,919, all assigned to Otsuka Pharmaceutical Co., Japan.

Cohen et al. describe the use of a series of aminoindans for the treatment of Parkinson's disease, dementia, epilepsy, convulsions or seizures and neurotrauma and disclose the preparation of certain novel representatives of that class. (U.S. Pat. Nos. 5,877,221; 5,880,159; 5,877,218).

SUMMARY OF THE INVENTION

The subject invention describes a method of treating mania in the bipolar mood disorder in a subject comprising administering to the subject a therapeutically effective amount of derivatives of 1-aminoindan, their racemic mixtures, enantiomers, and salts thereof, of the general formula:

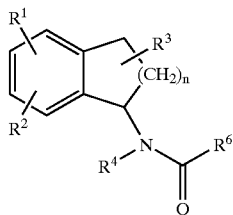

wherein n is 0 or 1;
each of $R^1$ and $R^2$ are hydrogen, $C_1$–$C_4$ alkyl, halogen;
$R^3$ is hydrogen, $C_1$–$C_4$ alkyl, hydroxy, $C_1$–$C_4$ alkoxy;
$R^4$ is hydrogen, $C_1$–$C_4$ alkyl;
$R^6$ is hydrogen, substituted or unsubstituted $C_1$–$C_{12}$ alkyl, $C_6$–$C_{12}$ aryl, $C_7$–$C_{12}$ aralkyl or A—N—$R^9R^{10}$, provided that $R^6$ is not methyl when $R^1$, $R^2$, $R^3$ and $R^4$ are hydrogen atoms,
wherein A is substituted or unsubstituted $C_1$–$C_{12}$ alkyl, substituted or unsubstituted $C_6$–$C_{12}$ aryl, substituted or unsubstituted $C_7$–$C_{12}$ aralkyl, and each of $R^9$ and $R^{10}$ are independently hydrogen, $C_1$–$C_{12}$ alkyl, $C_6$–$C_{12}$ aryl, $C_7$–$C_{12}$ aralkyl, COOtBu, or indanyl;
and racemic mixtures, enantiomers, and salts thereof.

DESCRIPTION OF THE FIGURES

FIGS. 2A–5B hereinafter describe the means ±SE for activity counts measured for each group for 30 minutes, at 10 minute time intervals. The asterisk "*" denotes a significant difference from the control. Drug administration is interperitoneal (IP).

FIG. 2A shows the locomotor activity level for rats which have been administered (R)-N-acetyl aminoindan (1) as compared to the control.

FIG. 5B shows the vertical activity level for rats which have been administered (S)-N-formyl aminoindan (4) as compared to the control.

DETAILED DESCRIPTION OF THE INVENTION

Figure 1:
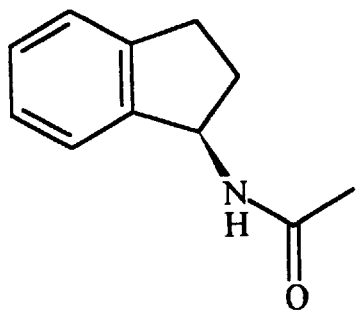
FIG. 1 shows four specific compounds discussed in the experiments: (R)-N-acetyl aminoindan (1), (S)-N-indanyl glycinamide HCl (2), (rac)-N-(2-aminoacetyl)-1-aminoindan HCl (3), (S)-N-formyl aminoindan (4).
Figure 1:
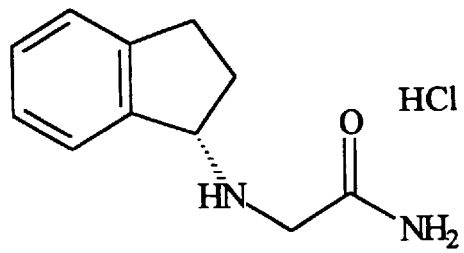
Figure 1:
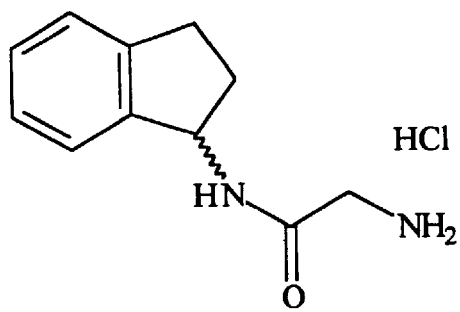
Figure 1:
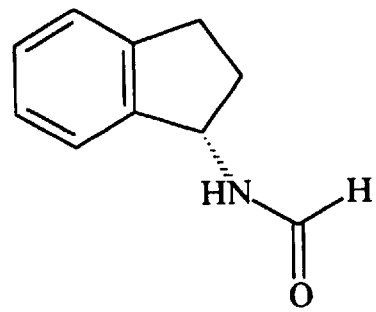

It has now been surprisingly observed that a particular class of 1-aminoindan derivatives decrease the amphetamine-induced hyperactivity levels while another class increases this hyperactivity.

This invention provides a method for the treatment of mania in bipolar mood disorder using derivatives of 1-aminoindan or their racemic mixtures, enantiomers, and salts thereof.

In particular, the present invention discloses a method of treating mania in bipolar mood disorder in a subject comprising administering to the subject a therapeutically effective amount of a compound of the formula:

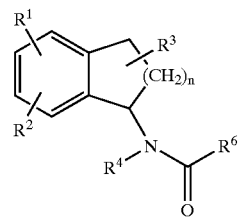

wherein n is 0 or 1;
each of $R^1$ and $R^2$ are hydrogen, $C_1$–$C_4$ alkyl, halogen;
$R^3$ is hydrogen, $C_1$–$C_4$ alkyl, hydroxy, $C_1$–$C_4$ alkoxy;
$R^4$ is hydrogen, $C_1$–$C_4$ alkyl;
$R^6$ is hydrogen, substituted or unsubstituted $C_1$–$C_{12}$ alkyl, $C_6$–$C_{12}$ aryl, $C_7$–$C_{12}$ aralkyl or A—N—$R^9R^{10}$, provided that $R^6$ is not methyl when $R^1$, $R^2$, $R^3$ and $R^4$ are hydrogen atoms,
wherein A is substituted or unsubstituted $C_1$–$C_{12}$ alkyl, substituted or unsubstituted $C_6$–$C_{12}$ aryl, substituted or unsubstituted $C_7$–$C_{12}$ aralkyl, and each of $R^9$ and $R^{10}$ are independently hydrogen, $C_1$–$C_{12}$ alkyl, $C_6$–$C_{12}$ aryl, $C_7$–$C_{12}$ aralkyl, COOtBu, or indanyl;
and racemic mixtures, enantiomers, and salts thereof.

In another embodiment of the invention, the compound is selected from the group consisting of (R)-N-acetyl aminoindan, (rac)-N-2-aminoacetyl-1-aminoindan HCl and (S)-N-formyl aminoindan.

In one embodiment of the invention, the subject is a human subject.

In a further embodiment of the invention, the salt is selected from the group consisting of a hydrochloride salt, a mesylate salt, an ethylsulfonate salt, and a sulfate salt.

In a specific embodiment of the invention, the salt is a hydrochloride salt.

In one embodiment of the invention, the administration is selected from the group consisting of oral, intraperitoneal, parenteral, topical, transdermal, rectal, nasal, and buccal administration.

In yet another embodiment of the invention, the therapeutically effective amount is an amount from 30 mg/kg to 150 mg/kg.

In a further embodiment of the invention, the therapeutically effective amount is an amount from 30 mg/kg to 100 mg/kg.

In a preferred embodiment of the invention, the therapeutically effective amount is an amount from 30 mg/kg to 75 mg/kg.

Experimental Details

I. Synthesis of Compounds

Cohen et al. disclose the preparation of the (R)-1-aminoindan starting material, and certain novel representatives of aminoindan (U.S. Pat. Nos. 5,877,221; 5,880,159; 5,877,218). The R- and S-enantiomers of each compound may be obtained by optical resolution of the corresponding racemic mixtures. Such a resolution can be accomplished by any conventional resolution method also disclosed in Cohen et al.

II. Experimental Examples

Evaluation of possible anti-bipolar effects of compounds 1 to 4 was effected by an amphetamine-induced hyperactivity model of mania in rats. Each of the compounds was examined in a separate experiment and compared with a control group, treated with the same dose of amphetamine.

Twenty Sprague Dawley rats, weighing 200–250 g served for each of the four (4) experiments. Rats were housed in a colony room with constant temperature (22° C.), 12 h light/dark cycle and free access to food and water. Each experiment consisted of two groups (n=10 per group), one group was treated with the compound (1 to 4) and the other with vehicle solution. In experiments 1–4, the drugs were administered intraperitoneally (IP). All experimental procedures were conducted during the light phase of the light/dark cycle.

Amphetamine (0.5 mg/kg, sub-cutaneous (s.c.), diluted in de-ionized water) was injected into all rats (both groups of each experiment) immediately prior to behavioral testing. In experiments 1 to 4, compounds (R)-N-acetyl aminoindan (1); (S)-N-indanyl glycinamide HCl (2); (rac)-N-(2-aminoacetyl)-1-aminoindan HCl (3); and (S)-N-formyl aminoindan (4) were injected twice intraperitoneally (IP) at a dose of 75 mg/kg, 19 h and 3 h prior to behavioral testing in experiments. All compounds were suspended in a 5% methyl cellulose solution. The vehicle solution was administered to the control animals.

Immediately after amphetamine injection, rats were placed in automated activity monitors and their activity levels were scored every 10 minutes in the 30 minute time span for experiments 1 to 4. Activity scores included separate measurements of horizontal (locomotion) and of vertical (rearing) activity.

Statistical Analysis

Repeated ANOVA measurements were used to examine the effects of compounds 1 to 4 on locomotor and on vertical activity. One factor measured the treatment of the rats using compounds 1 to 4 or the control vehicle; the repeated measure factor was time (three 10 minute intervals). Post hoc LSD (least significant difference) tests were used to determine whether significant differences occurred in different time periods, where relevant.

A. (R)-N-acetyl Aminoindan (1)

Figure 2A:
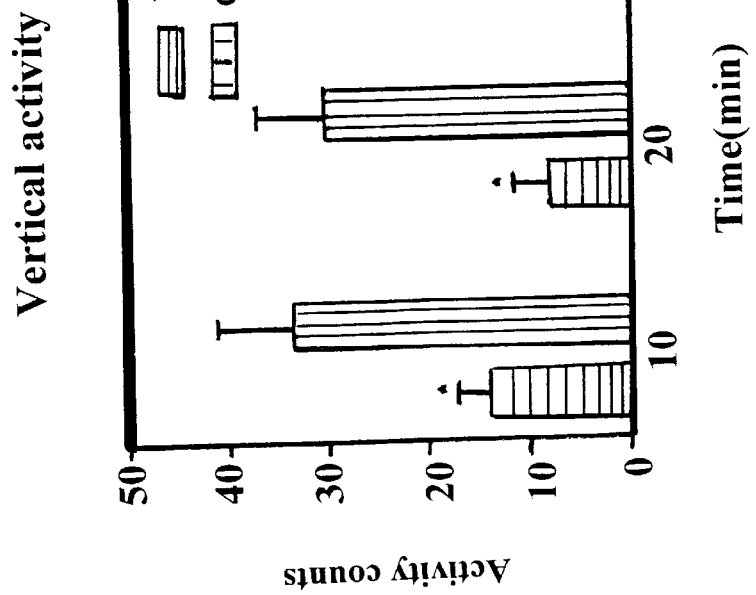
Figure 2B:
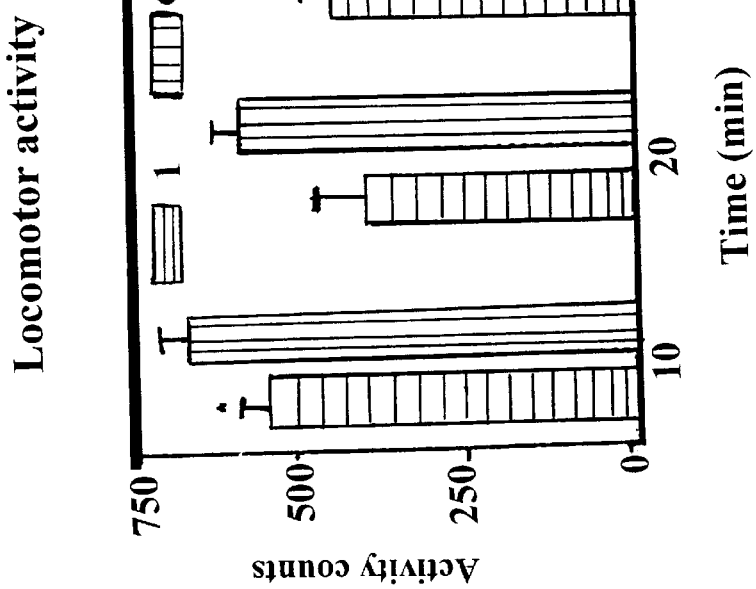
FIG. 2B shows the vertical activity level for rats which have been administered (R)-N-acetyl aminoindan (1) as compared to the control.

The results of the experiment employing (R)-N-acetyl aminoindan (1) are shown in Tables 1 and 2, as well as FIG. 2A and 2B. Table 1 compares the activity counts for rats which have been administered intraperitoneal (R)-N-acetyl aminoindan (1) to control rats for three 10 minute intervals. FIG. 2A shows the locomotor activity level for rats which have been administered intraperitoneally (R)-N-acetyl-aminoindan (1) as compared to the control. FIG. 2B shows the vertical activity level for rats which have been administered intraperitoneally (R)-N-acetyl-aminoindan (1) as compared to the control.

Subacute treatment with 75 mg/kg (R) -N-acetyl aminoindan significantly reduced locomotion following amphetamine treatment (FIG. 2A) (ANOVA: Drug effect: F(1)= 10.85, p<0.005; Time effect: F(2)=7.03, p<0.003; Interaction: F(2)=0.63, NS). Post hoc analysis indicates that the effect of the drug was significant at all time points (FIG. 2A). Similar effects were observed for vertical activity (ANOVA: Drug effect: F(1)=7.44, p<0.02; Time effect: F(2)=2.96, NS; Interaction: F(2)=2.32, NS). Post hoc analysis indicates significant differences during the first and second 10 minute time periods (FIG. 2B).

TABLE 1

Effect of (R)-N-acetyl aminoindan (1) on Activity Levels

| | 10 min | 20 min | 20-10 min | 30 min | 30-20 min |
|---|---|---|---|---|---|
| LOCOMOTOR ACTIVITY | | | | | |
| control | 830 | 1341 | 511 | 2026 | 685 |
| control | 723 | 1245 | 522 | 1899 | 654 |
| control | 810 | 1231 | 421 | 1727 | 496 |
| control | 565 | 1102 | 537 | 1525 | 423 |
| control | 569 | 1196 | 627 | 1798 | 602 |
| control | 551 | 1053 | 502 | 1640 | 587 |
| control | 687 | 1447 | 758 | 2091 | 644 |
| control | 606 | 1359 | 753 | 2067 | 708 |
| control | 496 | 1059 | 563 | 1428 | 369 |
| control | 850 | 1566 | 716 | 2295 | 729 |
| mean | 666.9 | 1259.9 | 591 | 1849.6 | 590 |
| std err | 40 | 52 | 36 | 86 | 38 |
| (1) | 600 | 930 | 330 | 1436 | 506 |
| (1) | 448 | 677 | 229 | 1027 | 350 |
| (1) | 718 | 1125 | 407 | 1653 | 528 |
| (1) | 740 | 1026 | 286 | 1317 | 291 |
| (1) | 570 | 1147 | 577 | 1776 | 629 |
| (1) | 426 | 802 | 376 | 1230 | 428 |
| (1) | 395 | 800 | 405 | 1053 | 253 |
| (1) | 462 | 794 | 332 | 1150 | 356 |
| (1) | 681 | 1361 | 680 | 2064 | 703 |
| (1) | 413 | 796 | 383 | 1250 | 454 |
| mean | 545.3 | 945.8 | 400.5 | 1395.6 | 449.8 |
| std err | 42 | 67 | 42 | 105 | 45 |
| VERTICAL ACTIVITY (cumulative and non cumulative counts) | | | | | |
| control | 80 | 115 | 35 | 132 | 17 |
| control | 29 | 48 | 19 | 52 | 4 |
| control | 40 | 47 | 7 | 52 | 5 |
| control | 10 | 19 | 9 | 31 | 12 |
| control | 34 | 76 | 42 | 120 | 44 |
| control | 9 | 19 | 10 | 31 | 12 |
| control | 27 | 92 | 65 | 112 | 20 |
| control | 25 | 66 | 41 | 79 | 13 |
| control | 14 | 29 | 15 | 34 | 5 |
| control | 69 | 130 | 61 | 179 | 49 |
| mean | 33.7 | 64.1 | 30.4 | 82.2 | 18.1 |
| std err | 8 | 12 | 7 | 16 | 5 |
| (1) | 27 | 34 | 7 | 62 | 28 |
| (1) | 9 | 12 | 3 | 18 | 6 |
| (1) | 16 | 18 | 2 | 20 | 2 |
| (1) | 29 | 29 | 0 | 31 | 2 |
| (1) | 20 | 37 | 17 | 53 | 16 |
| (1) | 16 | 28 | 12 | 38 | 10 |
| (1) | 5 | 12 | 7 | 12 | 0 |
| (1) | 10 | 11 | 1 | 21 | 10 |
| (1) | 6 | 39 | 33 | 76 | 37 |
| (1) | 4 | 5 | 1 | 7 | 2 |
| mean | 14.2 | 22.5 | 8.3 | 33.8 | 11.3 |
| std err | 3 | 4 | 3 | 7 | 4 |

B. (S)-N-indanyl Glycinamide HCl (2)

Figure 3B:
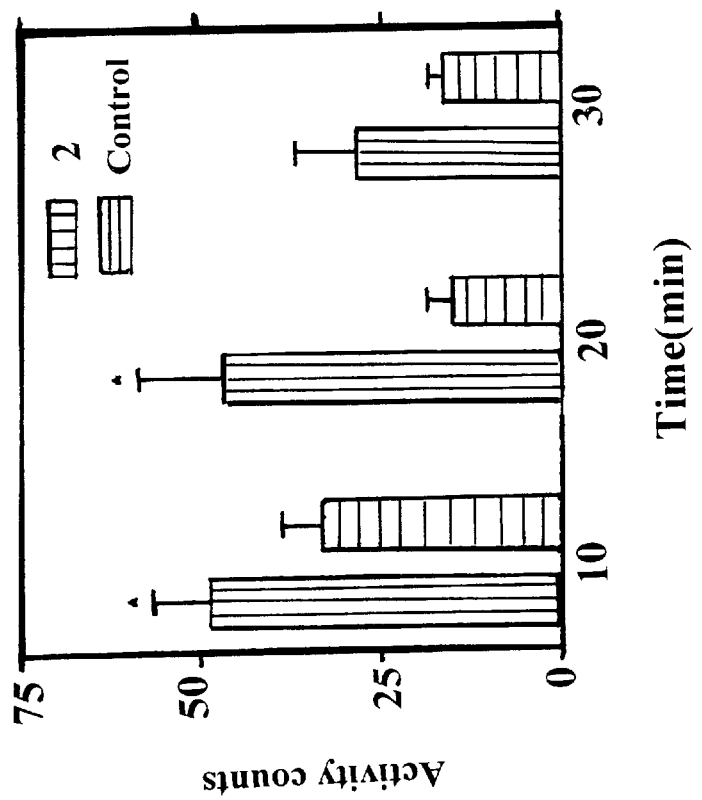
FIG. 3B shows the vertical activity level for rats which have been administered (S)-N-indanyl glycinamide HCl (2) as compared to the control.
Figure 3A:
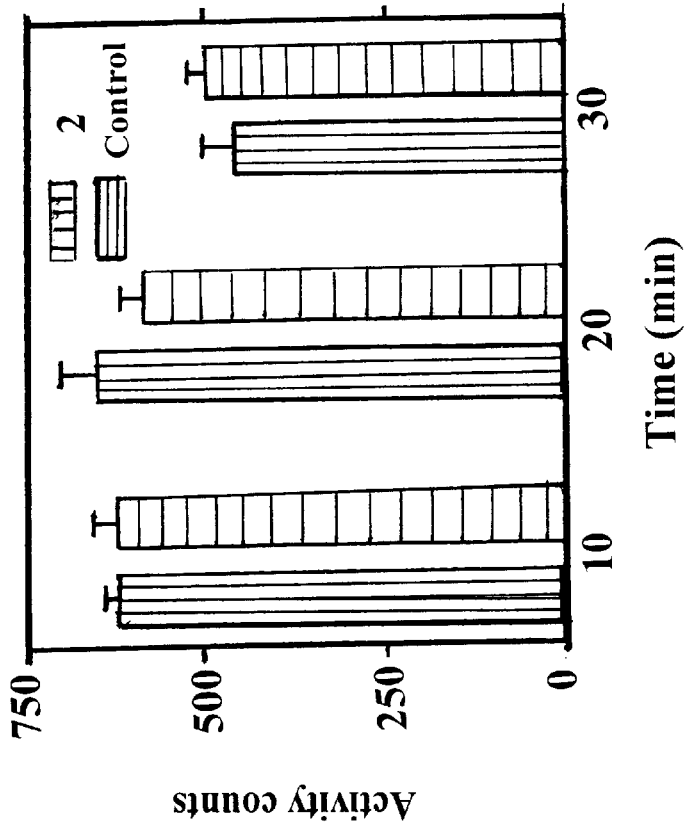
FIG. 3A shows the locomotor activity level for rats which have been administered (S)-N-indanyl glycinamide HCl (2) as compared to the control.

The results of the experiment employing (S) -N-indanyl glycinamide HCl (2) are shown in Table 2, FIG. 3A and FIG. 3B. Table 2 compares the activity counts for rats which have been administered (S)-N-indanyl glycinamide HCl (2) to control rats for three 10 minute intervals. FIG. 3A shows the locomotor activity level for rats which have been administered (S)-N-indanyl glycinamide HCl (2) as compared to the control. FIG. 3B shows the vertical activity level for rats which have been administered (S)-N-indanyl glycinamide HCl (2) as compared to the control.

Subacute treatment with (S)-N-indanyl glycinamide HCl (75 mg/kg) did not have a significant effect on amphetamine-induced locomotor activity (ANOVA: Drug effect: F(1)= 0.89, NS; Time effect: F(2)=15.923, p<0.001; Interaction: F(2)=1.5, NS; FIG. 3A). Contrary to expectations, the compound significantly increased the level of vertical activity (ANOVA: Drug effect: F(1)=5.499, p=0.031; Time effect: F(2)=8.533, p=0.001; Interaction: F(2)=2.537, NS). Post hoc analysis indicates that the difference between the groups was significant during the first and second 10 minute time periods (FIG. 3B).

TABLE 2

Effect of (S)-N-indanyl glycinamide HCl (2) on Activity Levels

| | 10 min | 20 min | 20-10 min | 30 min | 30-20 min |
|---|---|---|---|---|---|
| LOCOMOTOR ACTIVITY | | | | | |
| control | 560 | 1009 | 449 | 1487 | 478 |
| control | 604 | 1232 | 628 | 1719 | 687 |
| control | 504 | 1055 | 551 | 1560 | 505 |
| control | 466 | 920 | 454 | 1324 | 422 |
| control | 556 | 1233 | 677 | 1640 | 407 |
| control | 631 | 1205 | 574 | 1680 | 475 |
| control | 790 | 1572 | 782 | 2252 | 680 |
| control | 737 | 1328 | 591 | 1862 | 534 |
| control | 659 | 1273 | 614 | 1837 | 564 |
| control | 714 | 1275 | 561 | 1726 | 451 |
| mean | 622.1 | 1210.2 | 588.1 | 1708.7 | 520.3 |
| std err | 33 | 57 | 31 | 80 | 31 |
| (2) | 531 | 1096 | 565 | 1547 | 451 |
| (2) | 603 | 1197 | 594 | 1606 | 409 |
| (2) | 604 | 1334 | 730 | 1964 | 630 |
| (2) | 619 | 1140 | 521 | 1598 | 458 |
| (2) | 663 | 1525 | 862 | 1908 | 383 |
| (2) | 616 | 1508 | 892 | 2038 | 530 |
| (2) | 670 | 1366 | 696 | 1670 | 304 |
| (2) | 643 | 1272 | 629 | 1608 | 336 |
| (2) | 648 | 1325 | 677 | 2047 | 722 |
| (2) | 663 | 1016 | 353 | 1419 | 403 |
| mean | 626 | 1277.9 | 651.9 | 1740.5 | 462.6 |
| std err | 13 | 53 | 50 | 71 | 41 |
| VERTICAL ACTIVITY | | | | | |
| control | 35 | 41 | 6 | 57 | 16 |
| control | 26 | 38 | 12 | 46 | 8 |
| control | 24 | 59 | 35 | 73 | 14 |
| control | 7 | 8 | 1 | 25 | 17 |
| control | 10 | 14 | 4 | 19 | 5 |
| control | 40 | 62 | 22 | 91 | 29 |
| control | 42 | 70 | 28 | 89 | 19 |
| control | 41 | 50 | 9 | 61 | 11 |
| control | 44 | 60 | 16 | 80 | 20 |
| control | 65 | 86 | 21 | 111 | 25 |
| mean | 33.4 | 48.8 | 15.4 | 65.2 | 16.4 |
| std err | 5 | 8 | 3 | 9 | 2 |
| (2) | 32 | 51 | 19 | 75 | 24 |
| (2) | 82 | 133 | 51 | 168 | 35 |
| (2) | 31 | 62 | 31 | 98 | 36 |
| (2) | 38 | 84 | 46 | 96 | 12 |
| (2) | 38 | 101 | 63 | 104 | 3 |
| (2) | 95 | 236 | 141 | 321 | 85 |
| (2) | 66 | 118 | 52 | 126 | 8 |
| (2) | 38 | 50 | 12 | 58 | 8 |
| (2) | 30 | 70 | 40 | 116 | 46 |
| (2) | 43 | 58 | 15 | 88 | 30 |
| mean | 49.3 | 96.3 | 47 | 125 | 28.7 |
| std err | 7 | 18 | 12 | 23 | 8 |

C. (rac)-N-(2-Aminoacetyl)-1-aminoindan HCl (3)

Figure 4B:
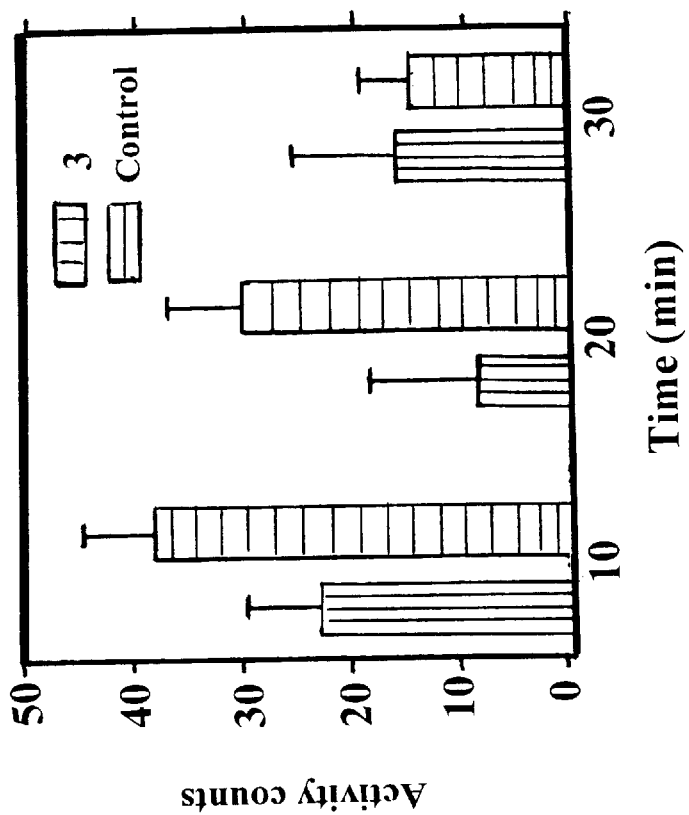
FIG. 4B shows the vertical activity level for rats which have been administered (rac)-N-(2-aminoacetyl)-1-aminoindan (3) as compared to the control.
Figure 4A:
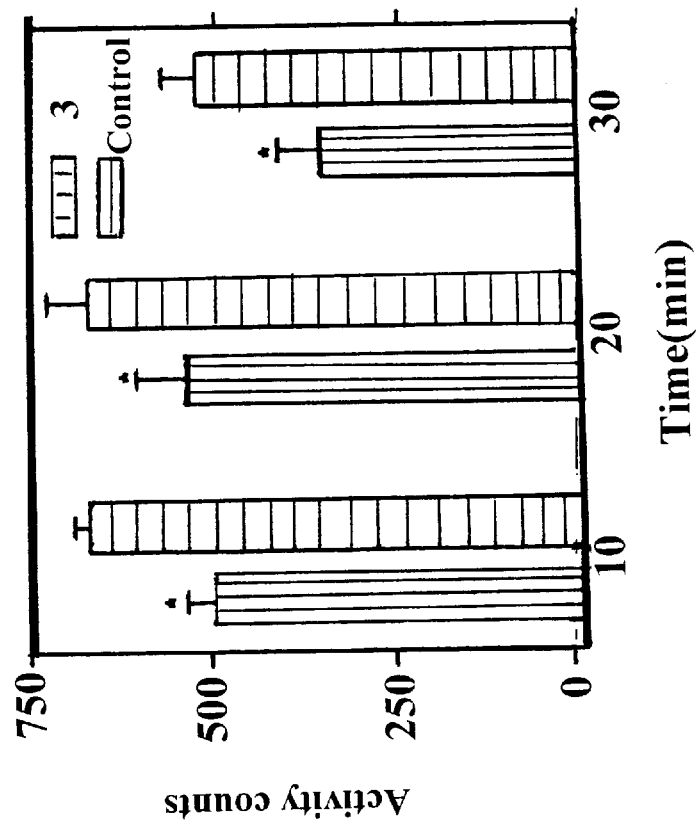
FIG. 4A shows the locomotor activity level for rats which have been administered (rac)-N-(2-aminoacetyl)-1-aminoindan (3) as compared to the control.

The results of the experiment employing (rac)-N-(2-aminoacetyl)-1-aminoindan HCl (3) are shown in Table 3, FIG. 4A and FIG. 4B. Table 3 compares the activity counts for rats which have been administered (rac)-N-(2-aminoacetyl)-1-aminoindan HCl (3) to control rats for three 10 minute intervals. FIG. 4A shows the locomotor activity level for rats which have been administered (rac)-N-(2-aminoacetyl)-1-aminoindan HCl (3) as compared to the control. FIG. 4B shows the vertical activity level for rats which have been administered (rac)-N-(2-aminoacetyl)-1-aminoindan HCl (3) as compared to the control.

Injections of (rac)-N-(2-aminoacetyl)-1-aminoindan HCl (75 mg/kg), 19 and 3 hours prior to testing significantly reduced locomotor activity of rats treated with amphetamine (ANOVA: Drug effect: F(1)=9.32, p<0.007; Time effect: F(2)=11.29, p<0.002; Interaction: F(2)=0.21, NS). Post hoc comparisons indicated that the difference was significant at all time periods (FIG. 4A). A similar, albeit non-significant, effect was demonstrated for vertical activity (FIG. 4B).

TABLE 3

Effect of (rac)-N-(2-aminoacetyl)-1-aminoindan HCl (3) on Activity Levels

| | 10 min | 20 min | 20-10 min | 30 min | 30-20 min |
|---|---|---|---|---|---|
| LOCOMOTOR ACTIVITY | | | | | |
| control | 713 | 1647 | 934 | 2101 | 454 |
| control | 685 | 1635 | 950 | 2138 | 503 |
| control | 580 | 990 | 410 | 1243 | 253 |
| control | 642 | 1303 | 661 | 1910 | 607 |
| control | 645 | 1246 | 601 | 1950 | 704 |
| control | 594 | 1164 | 570 | 1558 | 394 |
| control | 746 | 1470 | 724 | 2099 | 629 |
| control | 668 | 1442 | 774 | 2107 | 665 |
| control | 778 | 1414 | 636 | 2011 | 597 |
| control | 629 | 1090 | 461 | 1563 | 473 |
| mean | 668 | 1340 | 672.1 | 1868 | 527 |
| std err | 20 | 69 | 56 | 96 | 43 |
| (3) | 379 | 1214 | 835 | 1678 | 464 |
| (3) | 525 | 1196 | 671 | 1507 | 311 |
| (3) | 338 | 621 | 283 | 691 | 70 |
| (3) | 553 | 1303 | 750 | 1619 | 316 |
| (3) | 449 | 862 | 413 | 1112 | 250 |
| (3) | 349 | 663 | 314 | 917 | 254 |
| (3) | 584 | 1104 | 520 | 1576 | 472 |
| (3) | 614 | 1349 | 735 | 1810 | 461 |
| (3) | 537 | 1095 | 558 | 1758 | 663 |
| (3) | 616 | 963 | 347 | 1306 | 343 |
| mean | 494.4 | 1037 | 542.6 | 1397.4 | 360.4 |
| std err | 34 | 79 | 62 | 118 | 51 |
| VERTICAL ACTIVITY | | | | | |
| control | 47 | 99 | 52 | 110 | 11 |
| control | 44 | 62 | 18 | 64 | 2 |
| control | 25 | 28 | 3 | 28 | 0 |
| control | 3 | 75 | 72 | 94 | 19 |
| control | 42 | 76 | 34 | 117 | 41 |
| control | 23 | 43 | 20 | 53 | 10 |
| control | 66 | 113 | 47 | 141 | 28 |
| control | 18 | 28 | 10 | 28 | 0 |
| control | 59 | 78 | 19 | 107 | 29 |
| control | 55 | 82 | 27 | 93 | 11 |
| mean | 38.2 | 68.4 | 30.2 | 83.5 | 15.1 |
| std err | 6 | 9 | 7 | 12 | 4 |
| (3) | 0 | 0 | 0 | 1 | 1 |
| (3) | 17 | 33 | 16 | 35 | 2 |
| (3) | 7 | 11 | 4 | 11 | 0 |
| (3) | 27 | 91 | 64 | 101 | 10 |
| (3) | 11 | 26 | 15 | 35 | 9 |
| (3) | 5 | 5 | 0 | 5 | 0 |
| (3) | 36 | 66 | 30 | 75 | 9 |
| (3) | 58 | 1 | −57 | 100 | 99 |
| (3) | 16 | 21 | 5 | 38 | 17 |
| (3) | 54 | 66 | 12 | 82 | 16 |
| mean | 23.1 | 32 | 8.9 | 48.3 | 16.3 |
| std err | 6 | 10 | 9 | 12 | 9 |

D. (S)-N-formyl Aminoindan (4)

Figure 5B:
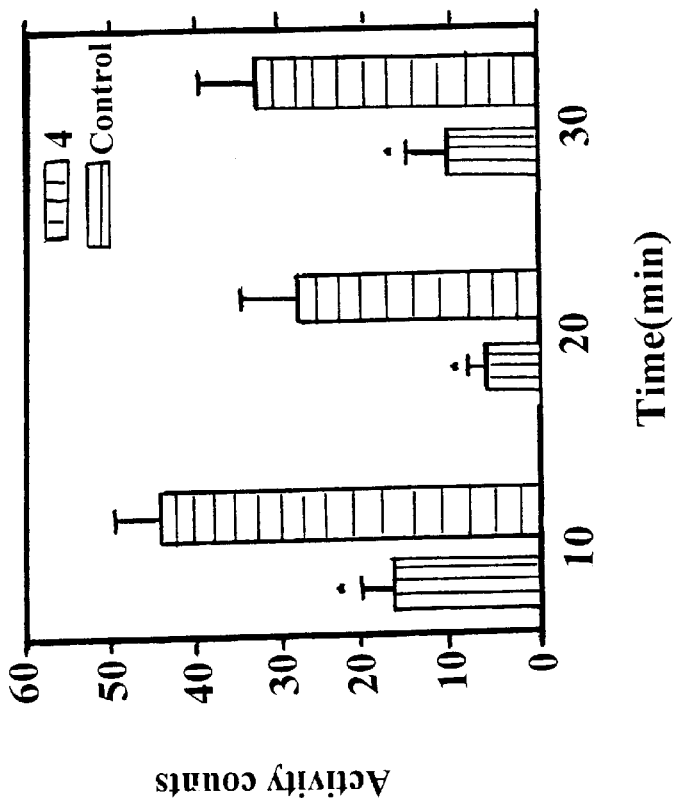
Figure 5A:
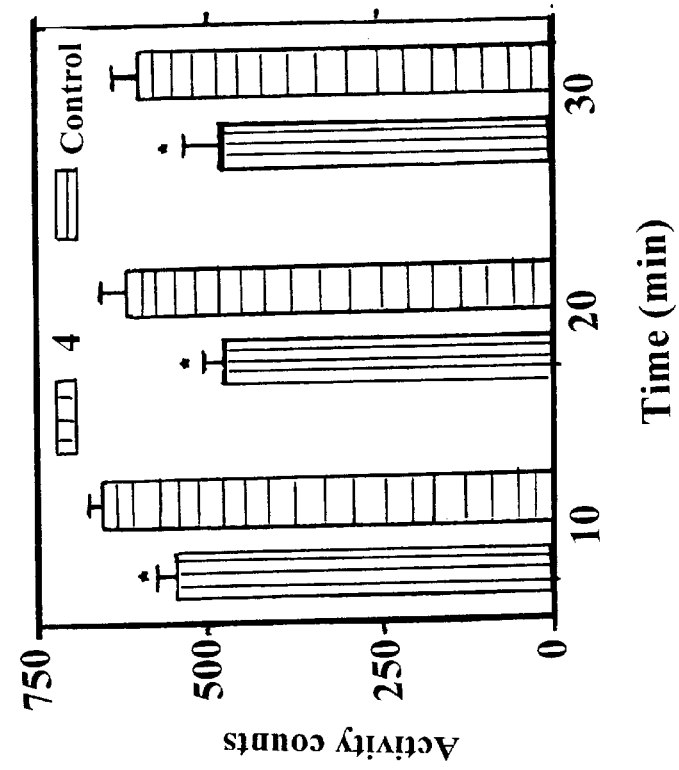
FIG. 5A shows the locomotor activity level for rats which have been administered (S)-N-formyl aminoindan (4) as compared to the control.

The results of the experiment employing (S)-N-formyl aminoindan (4) are shown in Table 4, FIG. 5A and FIG. 5B. Table 4 compares the activity counts for rats which have been administered (S)-N-formyl aminoindan (4) to control rats for three 10 minute intervals. FIG. 5A shows the locomotor activity level for rats which have been administered (S)-N-formyl aminoindan (4) as compared to the control. FIG. 5B shows the vertical activity level for rats which have been administered (S)-N-formyl aminoindan (4) as compared to the control.

(S)-N-formyl aminoindan significantly reduced amphetamine-induced locomotor activity (ANOVA: Drug effect: F(1)=8.18, p<0.011; Time effect: F(2)=5.2, p<0.011; Interaction: F(2)=0.42 NS) Post hoc analysis indicates difference at all time points (FIG. 5A). Similar significant effects were demonstrated for vertical activity (ANOVA: Drug effect: F(1)=14.1, p<0.002; Time effect: F(2)=10.64, p<0.0003; Interaction: F(2)=0.58, NS). Post hoc analysis indicated a difference at all time points (FIG. 5B).

TABLE 4

Effect of (S)-N-formyl aminoindan (4) on Activity Levels

|  | 10 min | 20 min | 20-10 min | 30 min | 30-20 min |
|---|---|---|---|---|---|
| LOCOMOTOR ACTIVITY | | | | | |
| control | 621 | 1167 | 546 | 1773 | 606 |
| control | 647 | 1426 | 779 | 2200 | 774 |
| control | 615 | 1294 | 679 | 1944 | 650 |
| control | 627 | 1034 | 407 | 1504 | 470 |
| control | 550 | 1029 | 479 | 1438 | 409 |
| control | 750 | 1497 | 747 | 2274 | 777 |
| control | 703 | 1374 | 671 | 1877 | 503 |
| control | 700 | 1363 | 663 | 2007 | 644 |
| control | 716 | 1347 | 631 | 1976 | 629 |
| control | 631 | 1244 | 613 | 1819 | 575 |
| mean | 656 | 1278 | 622 | 1881 | 604 |
| std err | 19 | 50 | 36 | 83 | 38 |
| (4) | 453 | 919 | 466 | 1371 | 452 |
| (4) | 589 | 1099 | 510 | 1632 | 533 |
| (4) | 482 | 896 | 414 | 1253 | 357 |
| (4) | 508 | 840 | 332 | 1031 | 191 |
| (4) | 596 | 1179 | 583 | 1789 | 610 |
| (4) | 558 | 1113 | 555 | 1730 | 617 |
| (4) | 481 | 923 | 442 | 1422 | 499 |
| (4) | 551 | 988 | 437 | 1422 | 434 |
| (4) | 691 | 1306 | 615 | 2061 | 755 |
| (4) | 619 | 1088 | 469 | 1519 | 431 |
| mean | 553 | 1035 | 482 | 1523 | 488 |
| std err | 23 | 46 | 27 | 92 | 49 |
| VERTICAL ACTIVITY | | | | | |
| control | 51 | 77 | 26 | 125 | 48 |
| control | 71 | 142 | 71 | 210 | 68 |
| control | 20 | 27 | 7 | 31 | 4 |
| control | 28 | 34 | 6 | 44 | 10 |
| control | 25 | 52 | 27 | 66 | 14 |
| control | 60 | 114 | 54 | 167 | 53 |
| control | 49 | 69 | 20 | 81 | 12 |
| control | 34 | 58 | 24 | 106 | 48 |
| control | 62 | 95 | 33 | 128 | 33 |
| control | 43 | 55 | 12 | 93 | 38 |
| mean | 44 | 72 | 28 | 105 | 33 |
| std err | 5 | 11 | 7 | 17 | 7 |
| (4) | 9 | 10 | 1 | 15 | 5 |
| (4) | 30 | 40 | 10 | 55 | 15 |
| (4) | 13 | 21 | 8 | 26 | 5 |
| (4) | 7 | 7 | 0 | 7 | 0 |
| (4) | 12 | 30 | 18 | 30 | 0 |
| (4) | 12 | 17 | 5 | 31 | 14 |
| (4) | 21 | 27 | 6 | 38 | 11 |
| (4) | 3 | 4 | 1 | 14 | 10 |
| (4) | 34 | 37 | 3 | 83 | 46 |
| (4) | 30 | 43 | 13 | 46 | 3 |
| mean | 17 | 24 | 7 | 35 | 11 |
| std err | 3 | 4 | 2 | 7 | 4 |

SUMMARY AND CONCLUSION

Significant effects on behavior were demonstrated in the present experiment for the compounds (R)-N-acetyl aminoindan (1), (S)-N-indanyl glycinamide HCl (2), (rac)-N-(2-aminoacetyl)-1-aminoindan HCl (3) and (S)-N-formyl aminoindan (4). Interestingly, while (R)-N-acetyl-aminoindan (1), (rac)-N-(2-aminoacetyl)-1-aminoindan HCl (3) and (S)-N-formyl aminoindan (4) reduced the activity levels of rats, by contrast, (S)-N-indanyl glycinamide HCl (2) surprisingly increased activity. From the tested model, the compounds (R)-N-acetyl aminoindan (1), (rac)-N-(2-aminoacetyl)-1-aminoindan HCl (3) and (S)-N-formyl aminoindan (4) show anti-manic potential in humans. The compound (S)-N-indanyl glycinamide HCl (2) does not show anti-manic potential based on the tested model and doses.

What is claimed is:

1. A method of treating mania in bipolar mood disorder in a subject comprising administering to the subject a therapeutically effective amount of a compound of the structure:

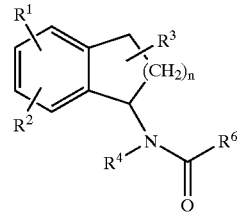

wherein n is 0 or 1;

each of $R^1$ and $R^2$ are hydrogen, $C_1$–$C_4$ alkyl, or halogen;

$R^3$ is hydrogen, $C_1$–$C_4$ alkyl, hydroxy, or $C_1$–$C_4$ alkoxy;

$R^4$ is hydrogen, or $C_1$–$C_4$ alkyl;

$R^6$ is hydrogen, substituted or unsubstituted $C_1$–$C_{12}$ alkyl, $C_6$–$C_{12}$ aryl, $C_7$–$C_{12}$ aralkyl or A—N—$R^9R^{10}$, provided that $R^6$ is not methyl when $R^1$, $R^2$, $R^3$ and $R^4$ are hydrogen atoms, wherein A is substituted or unsubstituted $C_1$–$C_{12}$ alkyl, substituted or unsubstituted $C_6$–$C_{12}$ aryl, or substituted or unsubstituted $C_7$–$C_{12}$ aralkyl, and each of $R^9$ and $R^{10}$ are independently hydrogen, $C_1$–$C_{12}$ alkyl, $C_6$–$C_{12}$ aryl, $C_7$–$C_{12}$ aralkyl, COOtBu, or indanyl;

or a racemic mixture, enantiomer, or salt thereof.

2. A method of treating mania in bipolar mood disorder in a subject comprising administering to the subject a therapeutically effective amount of a compound selected from the group consisting of (R)-N-acetyl aminoindan, (rac)-N-(2-aminoacetyl)-1-aminoindan HCl and (S)-N-formyl aminoindan.

3. The method of claim 1, wherein the subject is a human subject.

4. The method according to claim 1, wherein the compound is a salt selected from the group consisting of a hydrochloride salt, a mesylate salt, an ethylsulfonate salt, and a sulfate salt.

5. The method according to claim 4, wherein the salt is a hydrochloride salt.

6. The method according to claim 1, wherein the administration is selected from the group consisting of oral, intraperitoneal, parenteral, topical, transdermal, rectal, nasal, and buccal administration.

7. The method according to claim 1, wherein the therapeutically effective amount is an amount from 30 mg/kg to 150 mg/kg.

8. The method according to claim 7, wherein the therapeutically effective amount is an amount from 30 mg/kg to 100 mg/kg.

9. The method according to claim 8, wherein the therapeutically effective amount is an amount from 30 mg/kg to 75 mg/kg.

10. The method of claim 2, wherein the compound is (rac)-N-(2-aminoacetyl)-1-aminoindan HCl.

11. The method of claim 2, wherein the compound is (S)-N-formyl aminoindan.

12. The method of claim 2, wherein the compound is (R)-N-acetyl aminoindan.

13. The method according to claim 2, wherein the subject is a human subject.

14. The method according to claim 2, wherein the compound is a salt selected from the group consisting of a hydrochloride salt, a mesylate salt, an ethylsulfonate salt, and a sulfate salt.

15. The method according to claim 14, wherein the salt is a hydrochloride salt.

16. The method according to claim 2, wherein the administration is selected from the group consisting of oral, intraperitoneal, parenteral, topical, transdermal, rectal, nasal, and buccal administration.

17. The method according to claim 2, wherein the therapeutically effective amount is an amount from 30 mg/kg to 150 mg/kg.

18. The method according to claim 10, wherein the compound is a salt selected from the group consisting of a hydrochloride salt, a mesylate salt, an ethylsulfonate salt, and a sulfate salt.

19. The method according to claim 11, wherein the compound is a salt selected from the group consisting of a hydrochloride salt, a mesylate salt, an ethylsulfonate salt, and a sulfate salt.

20. The method according to claim 12, wherein the compound is a salt selected from the group consisting of a hydrochloride salt, a mesylate salt, an ethylsulfonate salt, and a sulfate salt.

* * * * *